United States Patent
Workman

(10) Patent No.: US 7,213,442 B2
(45) Date of Patent: May 8, 2007

(54) METHODS OF ARRANGING TRANSDUCERS AND TRANSDUCER ARRAYS HAVING REDUCED PHASE AMBIGUITY FOR DETERMINING DIRECTION OF ARRIVAL OF RECEIVED SIGNALS

(75) Inventor: Wayne C. Workman, St. Charles, MO (US)

(73) Assignee: The Boeing Company, Irvine, CA (US)

( * ) Notice: Subject to any disclaimer, the term of this patent is extended or adjusted under 35 U.S.C. 154(b) by 184 days.

(21) Appl. No.: 11/018,881

(22) Filed: Dec. 21, 2004

(65) Prior Publication Data

US 2006/0130555 A1    Jun. 22, 2006

Related U.S. Application Data

(63) Continuation-in-part of application No. 10/968,649, filed on Oct. 18, 2004.

(51) Int. Cl.
  *G01N 29/22* (2006.01)
  *G01S 5/04* (2006.01)
  *H01Q 21/06* (2006.01)
(52) U.S. Cl. .................. 73/1.82; 367/13; 342/424; 342/442; 342/444; 342/445; 342/446
(58) Field of Classification Search ............... 73/1.82; 367/13; 342/424, 442, 444, 445, 446
See application file for complete search history.

(56) References Cited

U.S. PATENT DOCUMENTS

| 5,574,468 | A | * | 11/1996 | Rose ........................ 342/442 |
| 5,657,027 | A | * | 8/1997 | Guymon, II ............... 342/445 |
| 5,936,575 | A |   | 8/1999 | Azzarelli et al. |
| 6,140,963 | A |   | 10/2000 | Azzarelli et al. |
| 6,195,043 | B1 |   | 2/2001 | Azzarelli et al. |
| 6,255,991 | B1 |   | 7/2001 | Hedin |
| 6,583,761 | B1 | * | 6/2003 | Angermeier et al. ........ 342/432 |
| 2001/0016505 | A1 | * | 8/2001 | Rexberg et al. ............ 455/562 |
| 2005/0076717 | A1 | * | 4/2005 | Chevret et al. .............. 73/649 |
| 2006/0119503 | A1 | * | 6/2006 | Allen et al. ................. 342/174 |

OTHER PUBLICATIONS

Hanson, J.E., "On Resolving Angle Ambiguities on n-Channel Interferometer Systems for Arbitrary Antenna Arrangements in a Plane," Defense Technical Information Center, Oct. 1973, 152 pages, NTIS, U.S. Department of Commerce.

* cited by examiner

*Primary Examiner*—Hezron Williams
*Assistant Examiner*—Rose M. Miller
(74) *Attorney, Agent, or Firm*—Senniger Powers

(57) ABSTRACT

Method of arranging transducers, including non-coplanar interferometer antennas on the outer surface of an aircraft, to minimize phase ambiguities when determining the direction of arrival of a signal received by an array of the transducers and emitted by a source remote from the array.

20 Claims, 12 Drawing Sheets

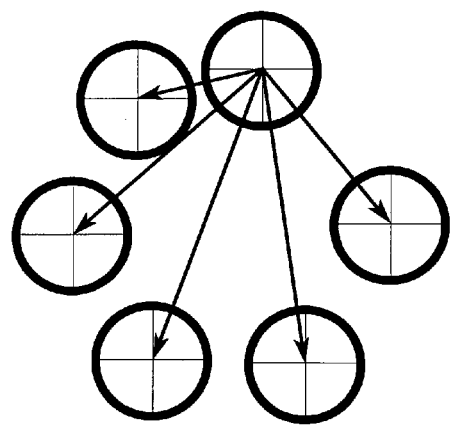
Figure 1a. A Circularly Composed Six Element Array
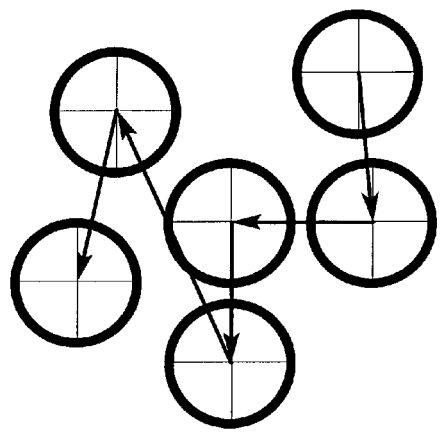
Figure 1b. A Square-Composed Six Element Array

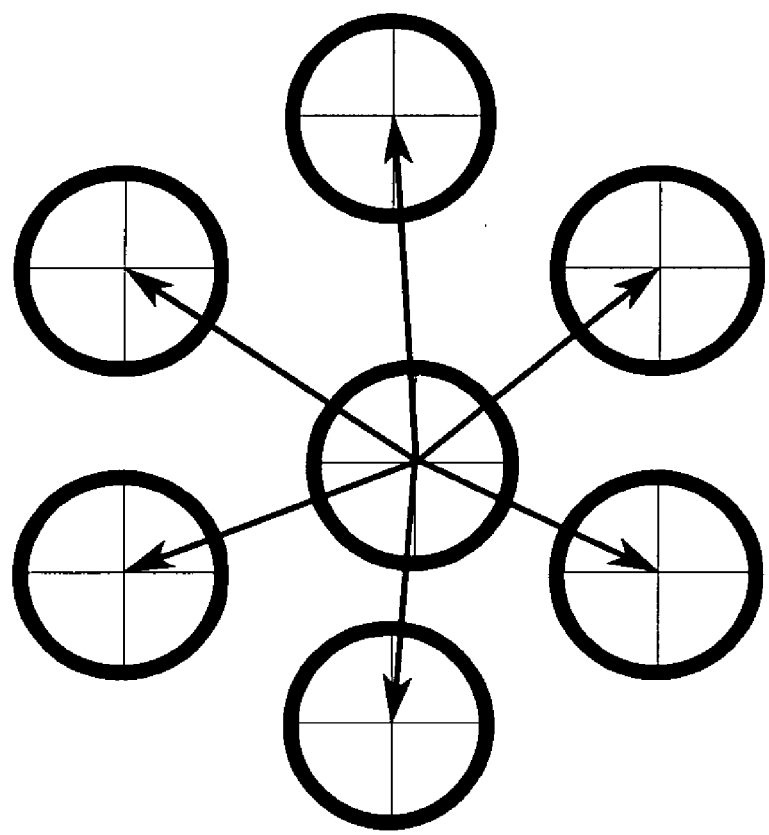
Figure 1c. A Hexagonally Composed Seven Element Array

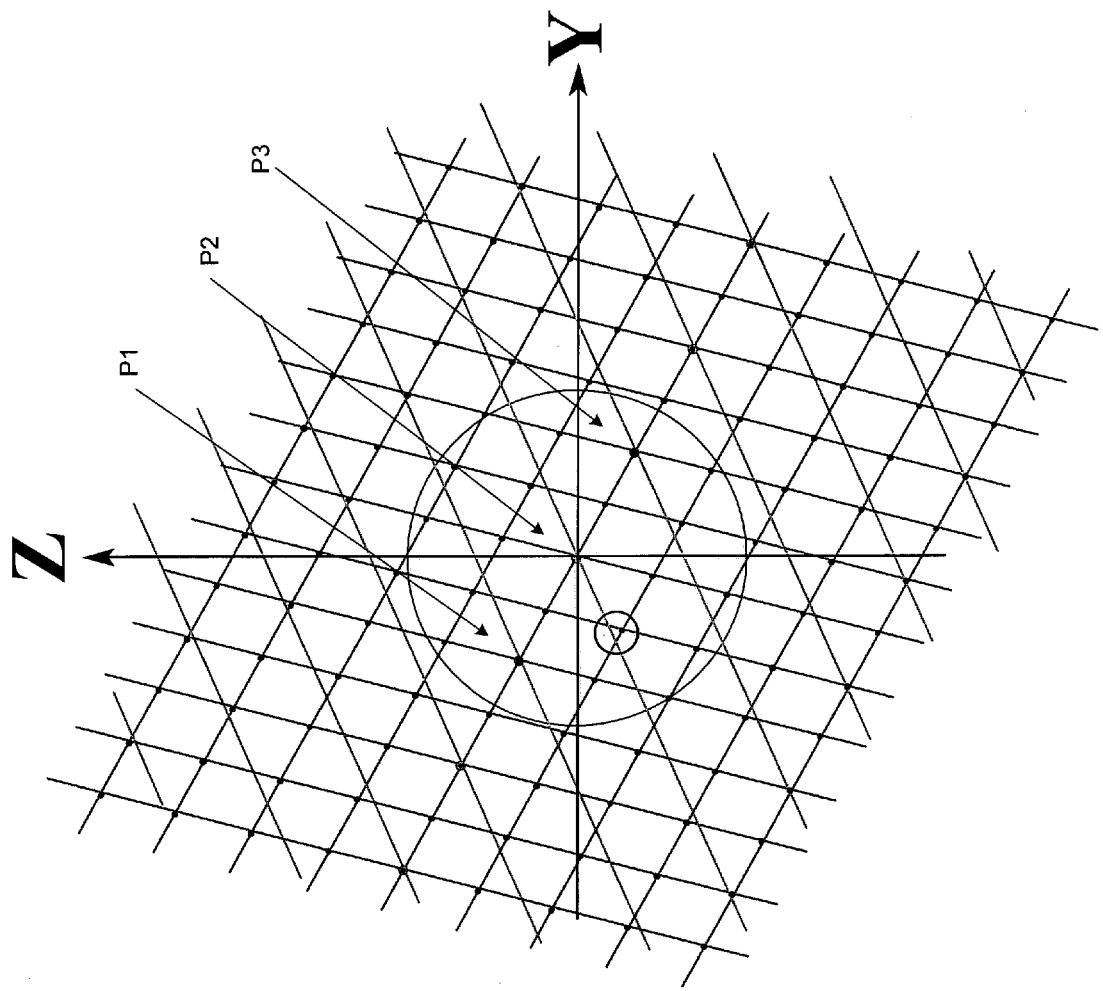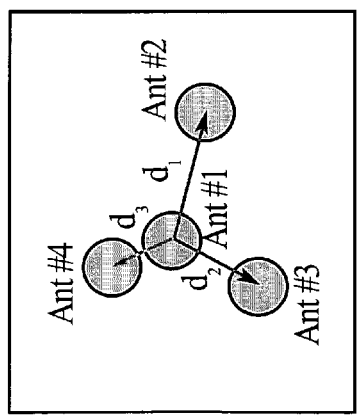
FIG. 4

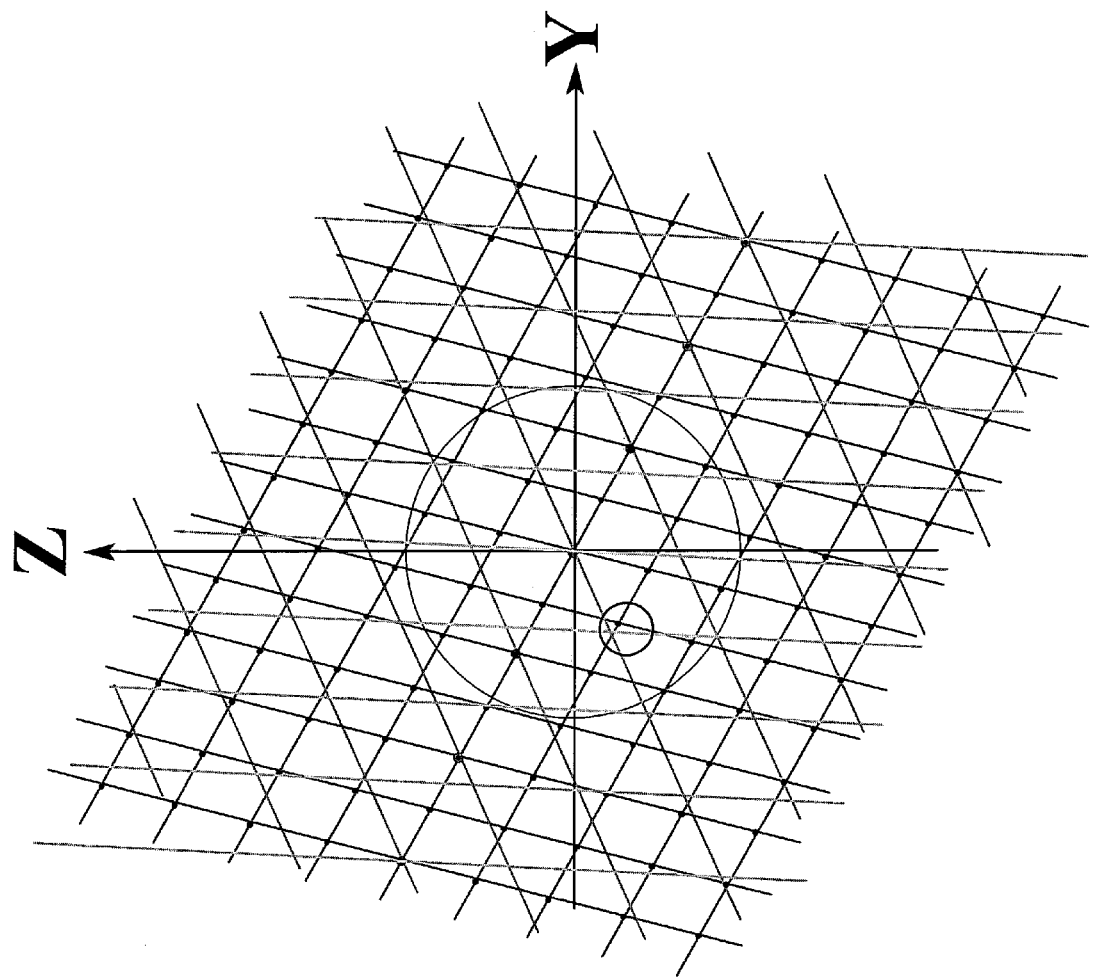
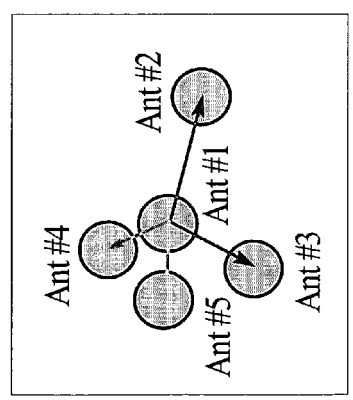
FIG. 5

METHODS OF ARRANGING TRANSDUCERS AND TRANSDUCER ARRAYS HAVING
REDUCED PHASE AMBIGUITY FOR
DETERMINING DIRECTION OF ARRIVAL
OF RECEIVED SIGNALS

FIELD OF THE INVENTION

This application is a continuation in part of U.S. patent application Ser. No. 10/968,649, invented by the same inventor as this application, filed Oct. 18, 2004, entitled SYSTEM AND METHOD FOR RESOLVING PHASE AMBIGUITY OF A TRANSDUCER ARRAY TO DETERMINE DIRECTION OF ARRIVAL OF RECEIVED SIGNALS which is incorporated by reference herein in its entirety.

The invention generally relates to transducer arrangements for direction finding systems. In particular, the invention includes a method for arranging transducers, including arranging non-coplanar interferometer antennas on the outer surface of an aircraft (submarine, ship, helicopter, truck, building, etc), to minimize phase ambiguities in order to the maximize the determination of direction of arrival or angle of arrival of a signal received by the array and emitted by a source remote from the array. The invention also relates to a method of arranging transducers, including non-coplanar interferometer antennas on the outer surface of an aircraft, to minimize phase ambiguities when determining the direction of arrival of a signal received by an array of the transducers and emitted by a source remote from the array.

BACKGROUND OF THE INVENTION

The arrangement of transducers in an array for an interferometric system is usually based on physical conveniences or other external considerations. Such systems may be used to determine direction of arrival of radiation received from a remote source. When used for this purpose, the arrangement can result in phase ambiguities which affect resolution.

The prior art contains several methods of phase ambiguity resolution for interferometric systems consisting of either collinear or non-collinear, coplanar arrangements of transducers, such as antennas.

In a treatise published in 1973 by James E. Hanson titled "On Resolving Angle Ambiguities of n-Channel Interferometer Systems for Arbitrary Antenna Arrangements In a Plane" (Defense Technical Information Center Publication Number AD 776-335) addresses ambiguities. In this treatise, Hanson demonstrated how the problem of interferometric phase ambiguity resolution could be easily approached by casting the several differential phase measurements into direction cosine space as a set of equally spaced parallel straight lines.

According to Hanson, phase ambiguity resolution is accomplished by finding an arrangement of three or more antennas that create a Hanson ambiguity diagram with but a single point of intersection of the various trajectories, an intersection that is located in direction cosine space at the exact position of the radiating source; for strictly collinear arrays of antennas the single intersection is rather a single straight line. It is also noted that this single point of intersection in direction cosine space leads immediately to the two angles of arrival—ϕ the azimuth angle and θ the zenith angle—so that ambiguity resolution leads to the determination of the angles of arrival.

The differential phase measurements made with practical interferometers come with errors that arise due to systematic as well as thermodynamic perturbations within the array antennas and the receiving network. These errors cause the Hanson trajectories to move or shift randomly at right angles to the directions in which they lay. As a consequence, in order to determine the single point of intersection in the ideal, no error condition becomes a set of pair-wise trajectory intersections. Thus, ambiguity resolution is accomplished by designing the ambiguity resolution computer algorithm so that it can discern a tightly grouped set of pair-wise intersections. Such an approach is described by Azzarelli, et al. in U.S. Pat. No. 6,140,963 but only for non-linear, coplanar arrays.

However, there is a need for a system and method which deal with the arrangement of transducers and particularly non-coplanar arrangements of antenna elements in order to minimize phase ambiguities and in order to maximize the determination of direction of arrival or angle of arrival of a signal received by the arrangements and emitted by a source remote from the arrangements. In addition, there is a need for a method which minimizes the phase errors that arise due various perturbations.

SUMMARY OF THE INVENTION

The invention includes a method for arranging transducers to resolve the angular ambiguities inherent in the differential phase measurements of an interferometric system of non-coplanar antennas. The method is also applicable to other transducer systems, such as an underwater sonar system of sonaphonic transducers or a seismic system of acoustic wave transducers or pressure transducers used for oil field exploration. For example, the transducers may be any of the following: antennas, RF sensors, sonaphones, sound sensors, seismic sensors, acoustic wave sensors and/or pressure sensors. Those skilled in the art will recognize other types of transducer arrays to which the invention is applicable. In general, the invention is applicable to arranging any array having phase ambiguity.

In one form, the invention comprises a method of arranging a plurality of spaced transducers having phase errors in order to determine a direction of arrival of a signal (radiation) emitted by a source. The method comprises:

determining a set of trajectories for a preset number of the plurality of transducers and determining the number of ambiguities corresponding to the set of trajectories;

modifying the preset number of the transducers;

determining a modified set of trajectories for the plurality of transducers after modifying the preset number and determining the number of ambiguities corresponding to the modified set of trajectories;

comparing the number of ambiguities corresponding to the set of trajectories to the number of ambiguities corresponding to the modified set of trajectories to determine the more tightly grouped set of trajectories; and arranging an array of the transducers having a number of transducers which corresponds to the set with less ambiguities.

In another form, the invention comprises a method of arranging a plurality of spaced transducers having phase errors in order to use the transducers to determine a direction of arrival of a signal (radiation) emitted by a source. The method comprises:

determining a set of trajectories for the plurality of transducers and determining the number of ambiguities corresponding to the set of trajectories;

modifying the relative position of the transducers;

determining a modified set of trajectories for the plurality of transducers after modifying the position and determining the number of ambiguities corresponding to the modified set of trajectories;

comparing the number of ambiguities corresponding to the set of trajectories to the number of ambiguities corresponding to the modified set of trajectories; and arranging the transducers according the position which corresponds to less ambiguities.

Other objects and features will be in part apparent and in part pointed out hereinafter.

BRIEF DESCRIPTION OF THE DRAWINGS

Having thus described the invention in general terms, reference will now be made to the accompanying drawings wherein:

FIGS. 1A, 1B and 1C illustrate three hypothetical coplanar arrays, each of which require complex analytic methods for deciding individual antenna placement within the respective array structure in order to ensure operation without irresolvable angle ambiguities.

Figure 2:
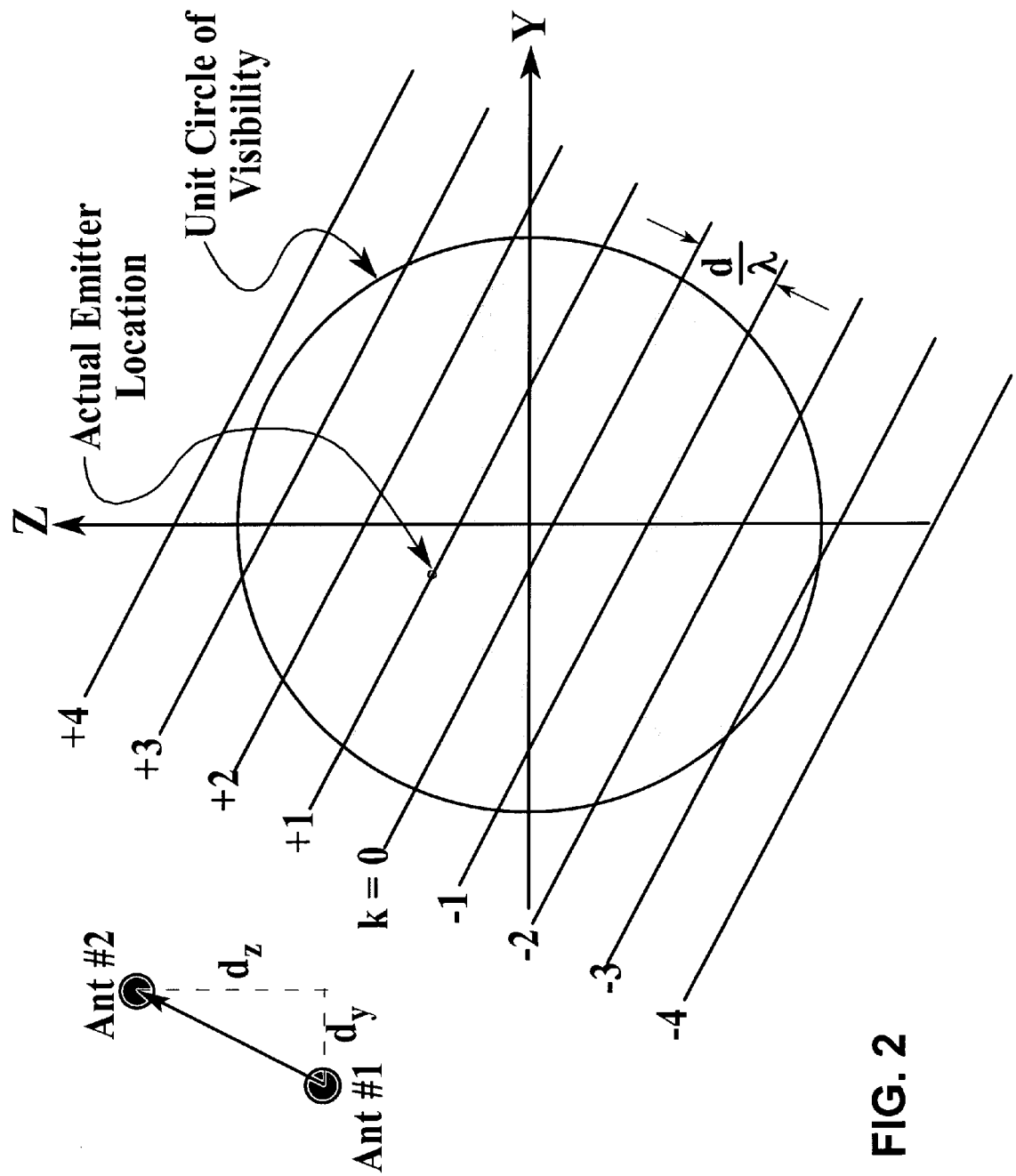

FIG. 2 is the Hanson Ambiguity Diagram for the pair of interferometer elements shown in the inset in the upper left corner.

Figure 3:
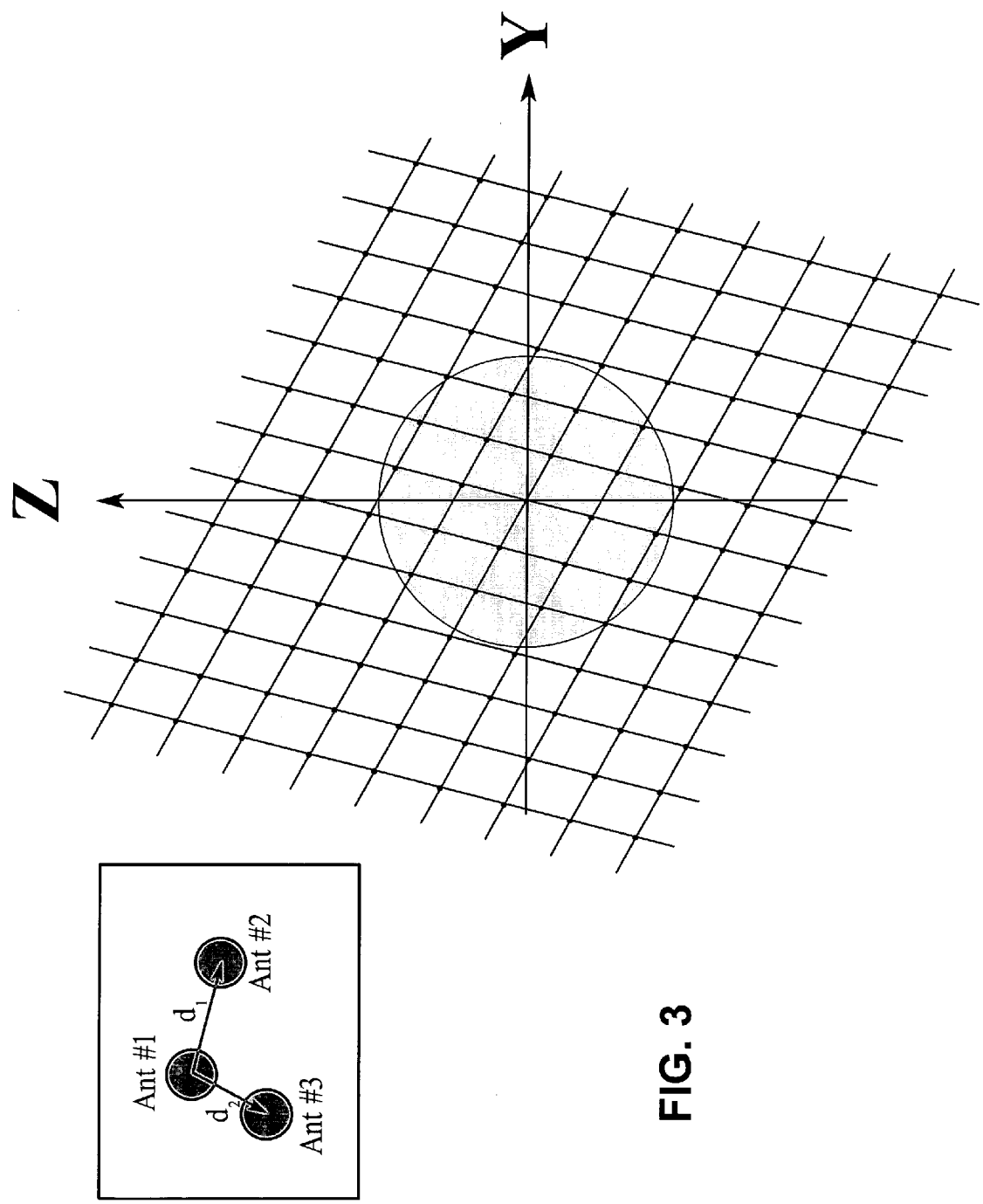

FIG. 3 illustrates the lattice of points created by the intersection of two sets of Hanson ambiguity trajectories of the two antenna pairs illustrated in the inset in the upper left corner.

FIG. 4 illustrates the Hanson ambiguity diagram for the four element interferometer array in the inset in the upper left corner showing that the nineteen irresolvable angle ambiguities seen in FIG. 3 have been reduced to only three points P1, P2, P3 by the addition of the fourth antenna.

FIG. 5 is the Hanson ambiguity diagram for the completed interferometer design for the five element interferometer array in the inset in the upper left corner that exhibits no irresolvable angle ambiguities inside the unit circle of visibility.

Figure 6:
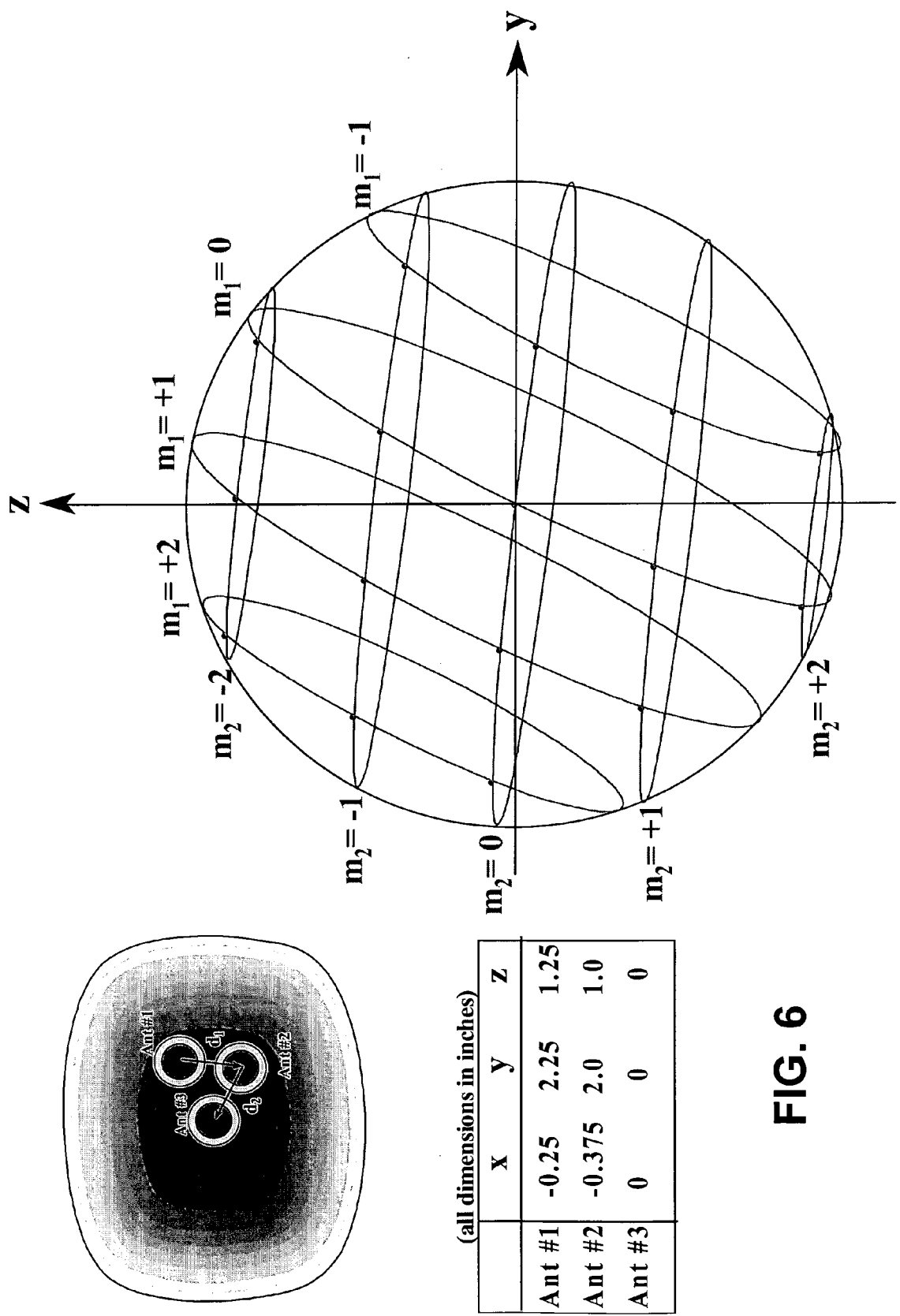

FIG. 6 illustrates the Hanson-Workman ambiguity diagram for three antennas arranged as illustrated in the inset schematic diagram and as indicated in the table.

Figure 7:
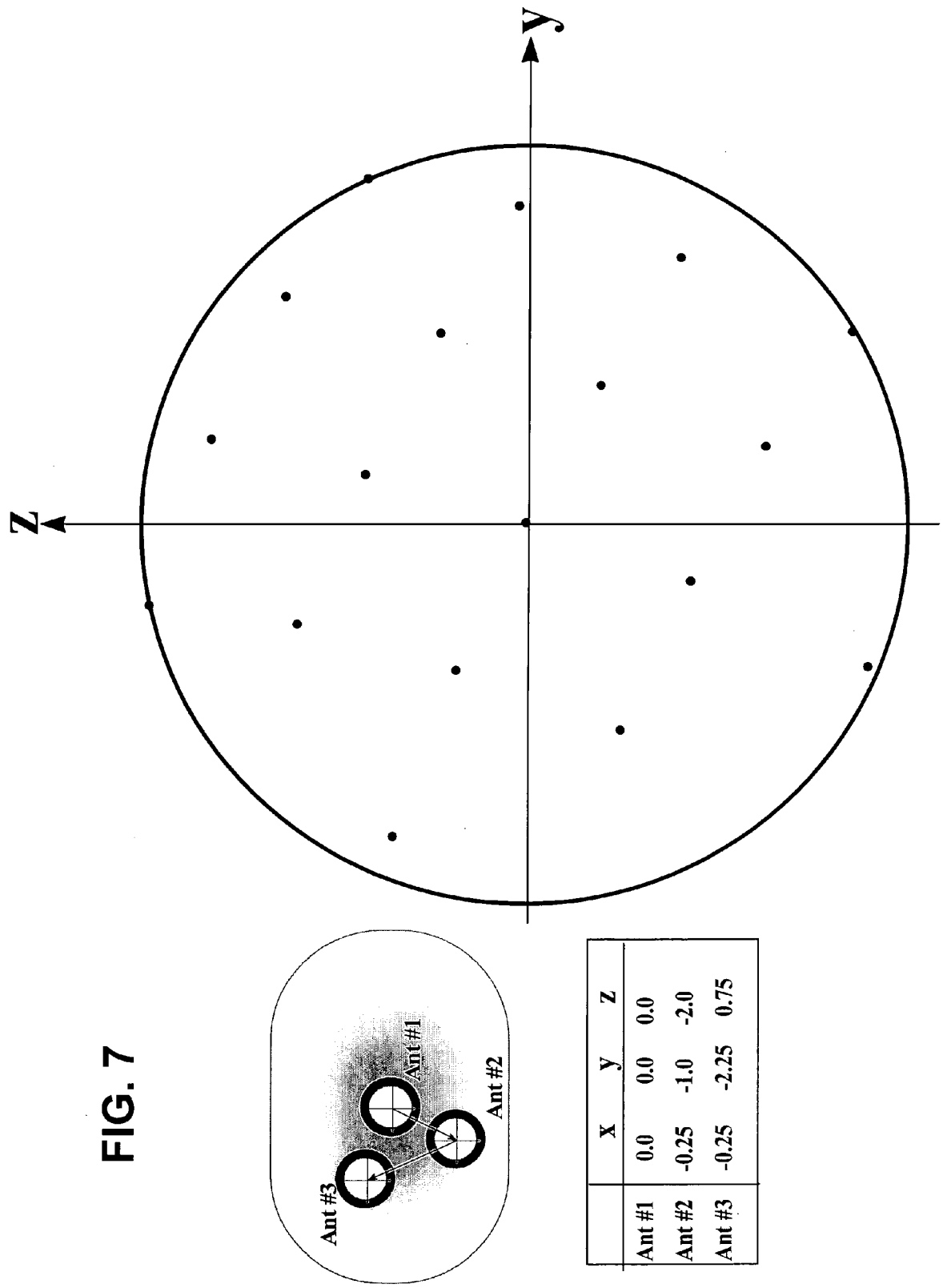

FIG. 7 illustrates the Hanson-Workman ambiguity diagram for the three element non-coplanar test array in the inset that will serve as the basis for illustrating the design process which results in an unambiguous interferometer array.

Figure 8:
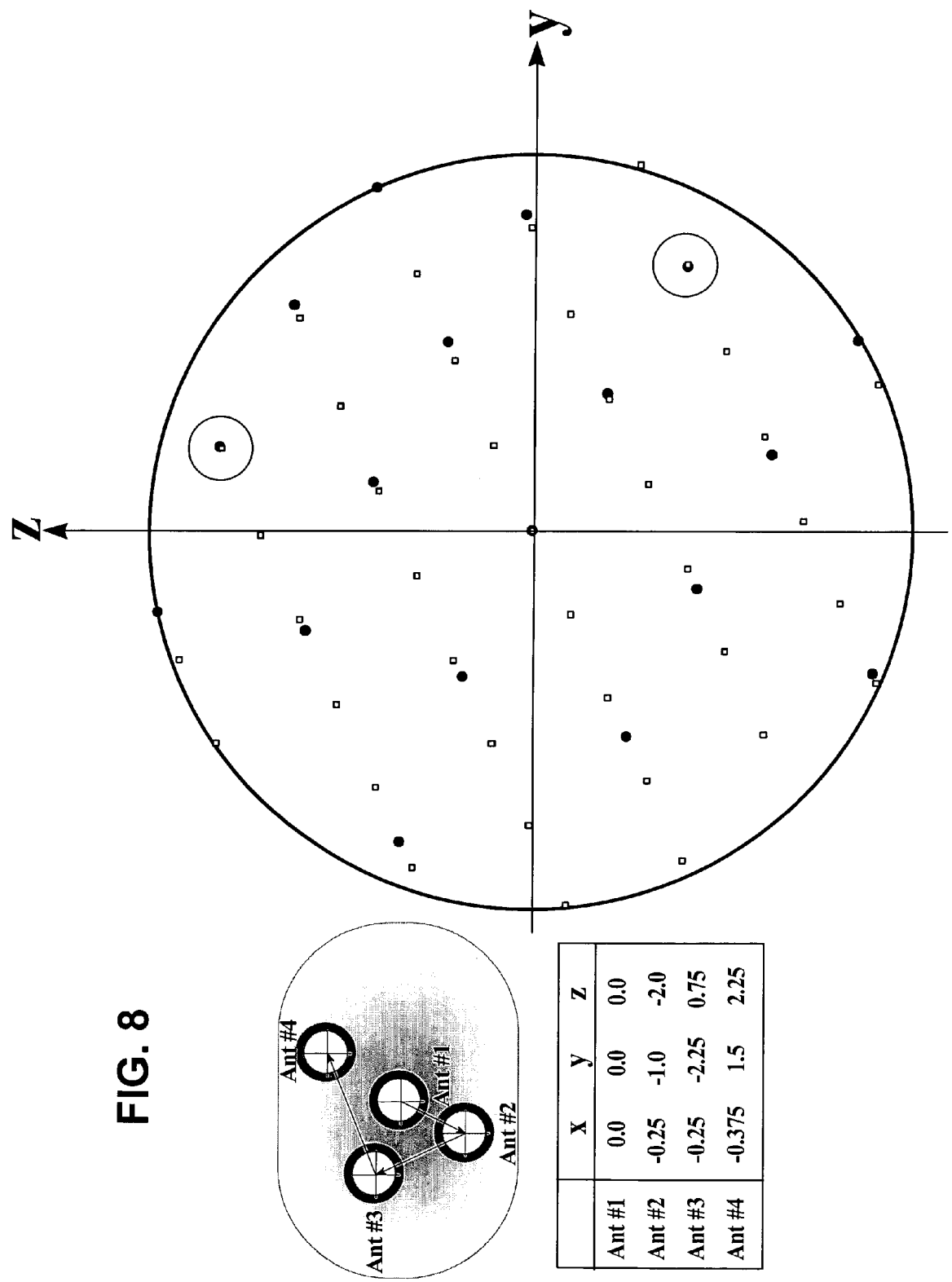

FIG. 8 illustrates adding antenna #4 to the three element array of FIG. 7 resulting in two irresolvable angle ambiguities (circled) and ten troublesome near-miss pairs.

Figure 9:
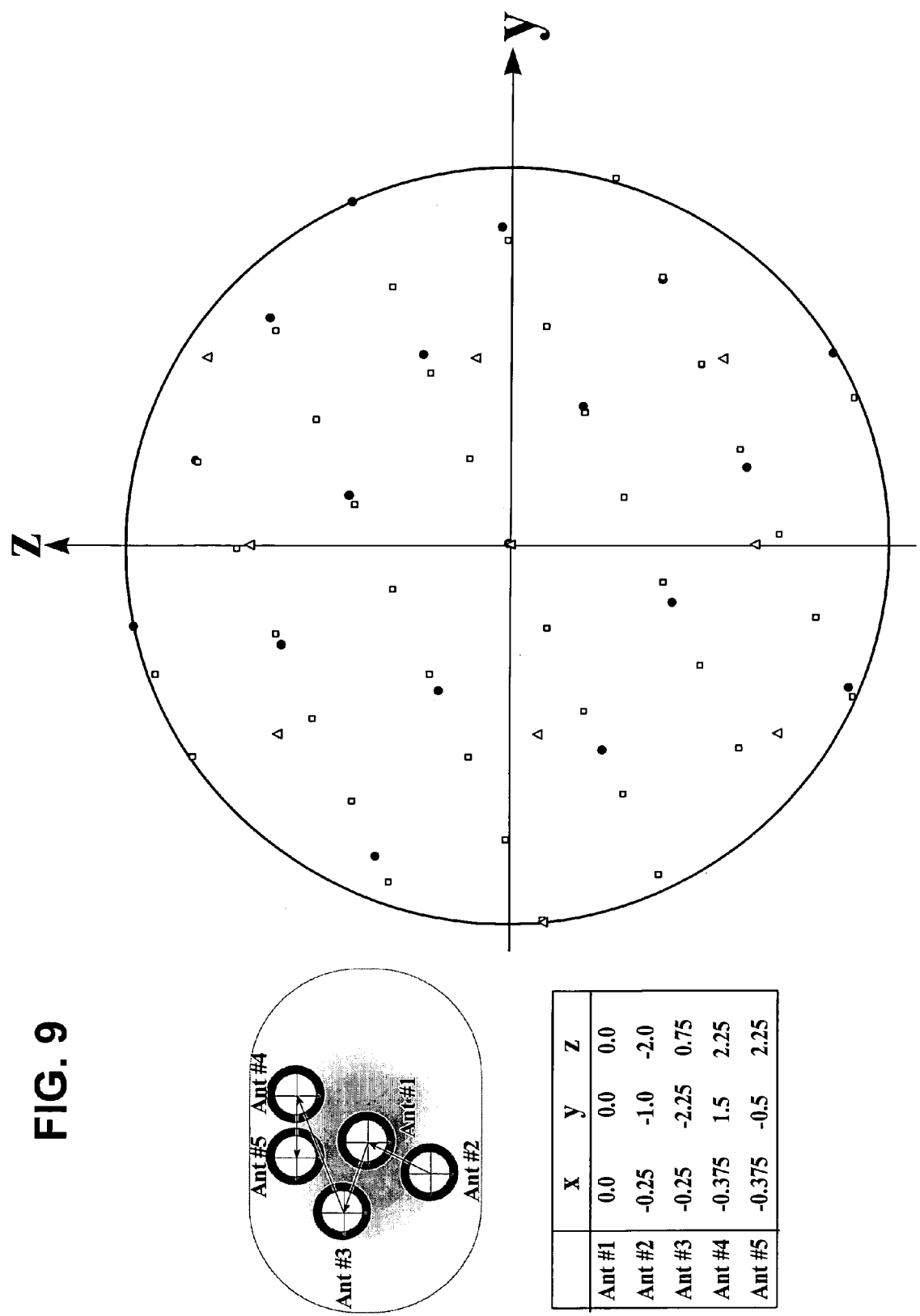

FIG. 9 illustrates adding the fifth element to the array eliminating the two irresolvable ambiguities depicted in FIG. 8 as well as all near-miss pairs without reintroducing any additional irresolvable ambiguities.

Figure 10:
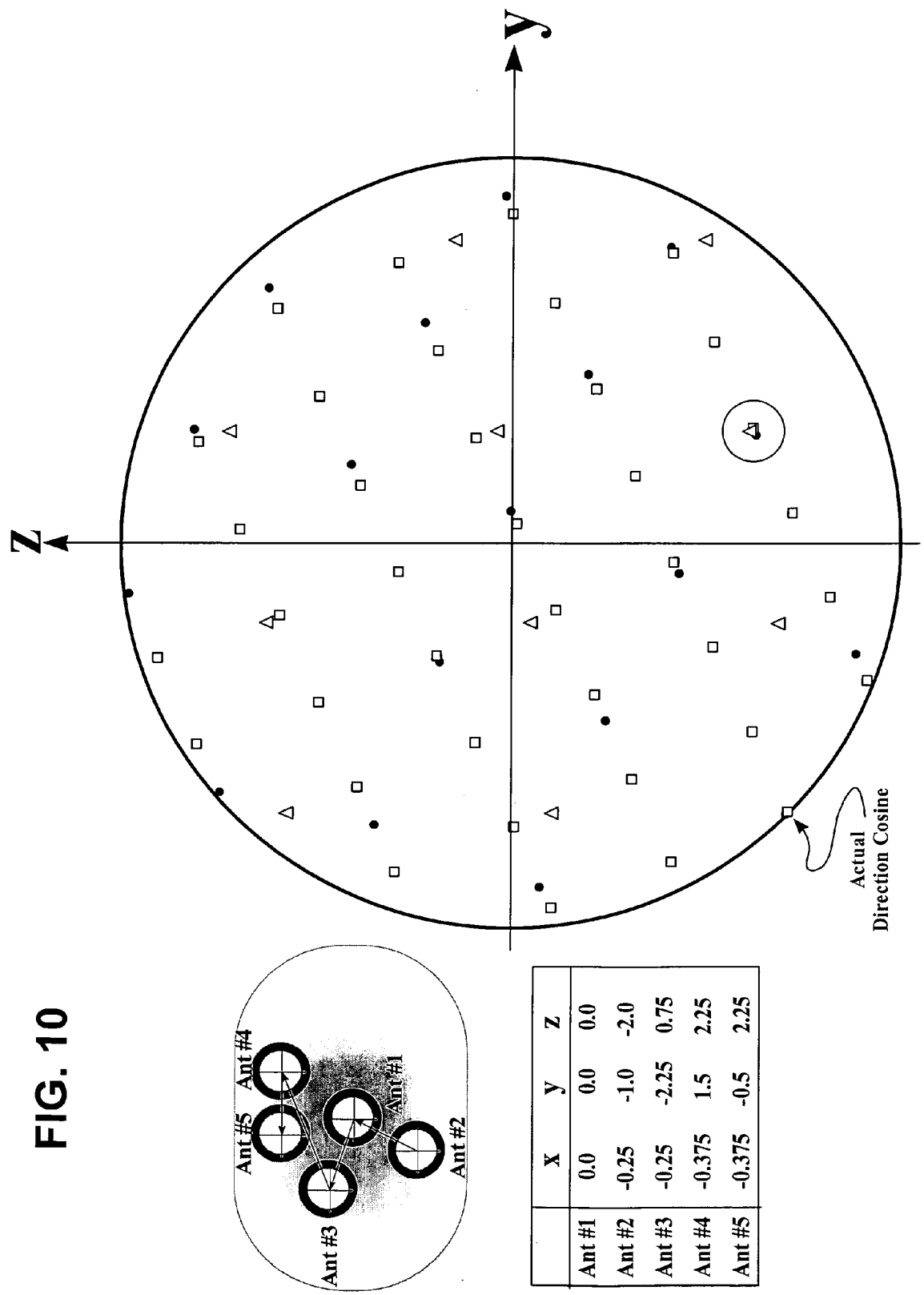

FIG. 10 illustrates the results of an "edge of field of view" test conducted to see if irresolvable ambiguities and/or near-miss clusters come into view as the direction of arrival angle is scanned away from the exact center of the y-z plane. One near-miss cluster (circled) was found.

Figure 11:
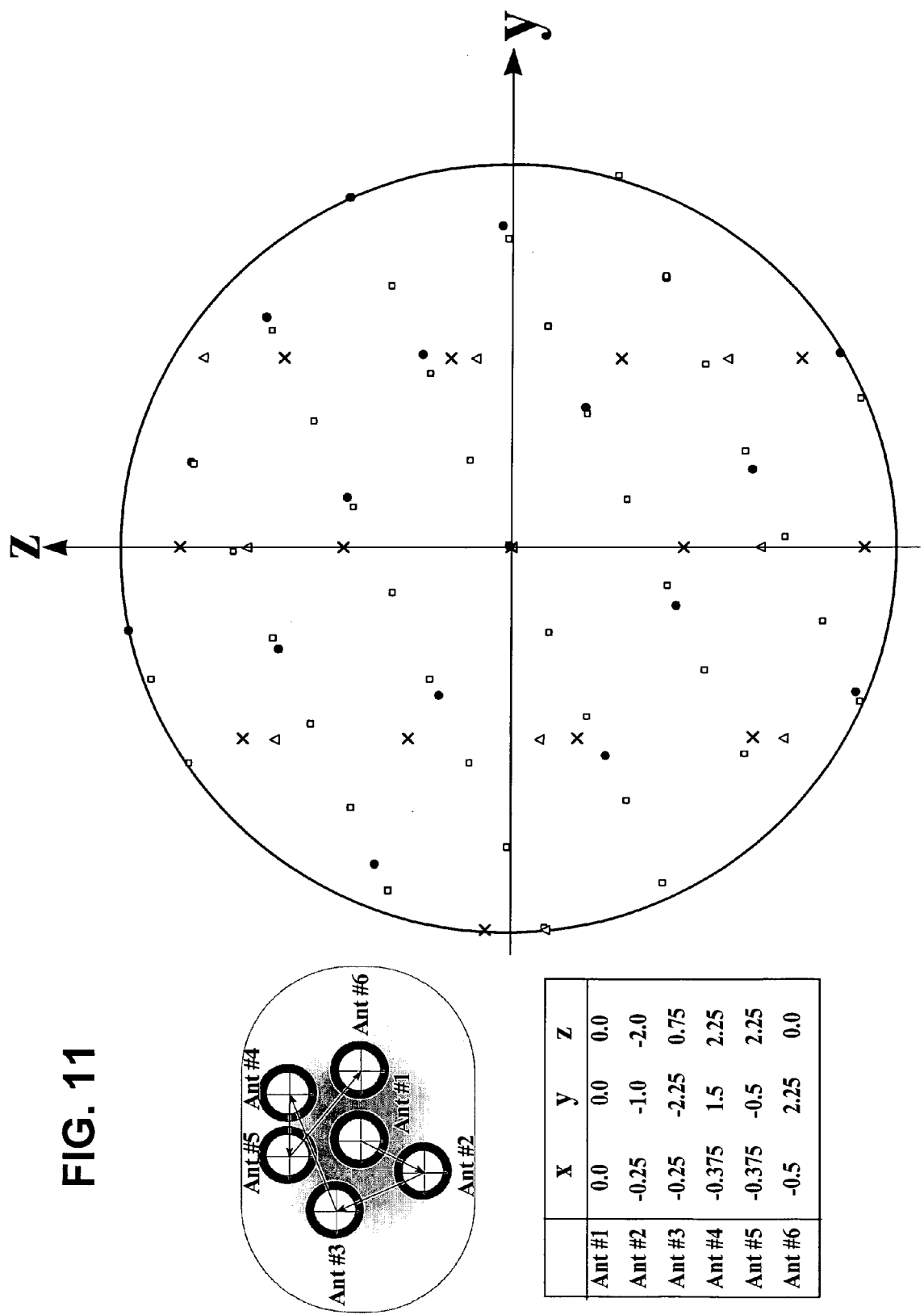

FIG. 11 illustrates the completed design of a six element interferometer array. The intersection points for the fourth and five baselines are depicted as an X.

Corresponding reference characters indicate corresponding parts throughout the drawings.

DETAILED DESCRIPTION OF THE PREFERRED EMBODIMENT

This invention relates to positioning transducers and particularly antennas to maximize the resolution of phase ambiguity and to minimize phase ambiguities according to the system and method of the first part.

This invention deals with phase comparison interferometry arrays. In particular, it describes a method for arranging the individual antenna elements within a non-coplanar array so that the array exhibits are no irresolvable angle ambiguities within visible space. When a phase comparison interferometer array exhibits such irresolvable angle ambiguities, its operational value could be greatly diminished.

Within the prior art interferometer designs consisting of three, four and five element collinear arrays as well as coplanar, non-collinear arrays of five six and seven antennas elements. The methods for deciding how many, where and how to place individual antenna elements within such arrays vary from the simple to the complex. Simple three element collinear arrays require little more than a simple, almost intuitive method of arranging the antennas in order to guarantee that no irresolvable angle ambiguities arise. On the other hand, coplanar, non-collinear arrays such as illustrated in FIGS. 1A, 1B and 1C demand a much more analytic approach to antenna placement.

FIGS. 1A, 1B and 1C illustrate three hypothetical coplanar arrays, each of which require complex analytic methods for deciding individual antenna placement within the respective array structure in order to ensure operation without irresolvable angle ambiguities. FIG. 1A illustrates a circularly arranged six (6) element array. FIG. 1B illustrates a squarely arranged six (6) element array. FIG. 1C illustrates a hexagonally arranged seven (7) element array.

For convenience within this application individual antenna elements are illustrated as circular apertures. Planar spirals, circular horns and several other elements available within the prior art are all examples of circular aperture antenna elements. However, phase comparison interferometers do not demand circular apertures. Square, rectangular and even irregularly shaped apertures have been successfully put to this purpose.

While non-coplanar interferometer arrays had previously been contemplated, until the recent submission of co-pending patent application Ser. No. 10/968,649, no effective method was known for resolving the many phase ambiguities that naturally arise from the phase difference measurements made amongst the several antennas of such an array. The methods and apparatus described in that patent application are incorporated herein.

One embodiment of an analytic method of the invention involves using the so-called Hanson ambiguity diagram. This Hanson ambiguity diagram is a geometrical concept based on the principals enunciated by Mr. James E. Hanson in his 1973 paper titled "On Resolving Angle Ambiguities of n-Channel Interferometer Systems for Arbitrary Antenna Arrangements In a Plane" (available through DTIC, DTIC number AD-776 335). To construct a Hanson ambiguity diagram for a complex array such as those illustrated in FIGS. 1A, 1B and 1C, it is first recognized that the phase difference between any two elements lying exclusively within the y-z plane can be expressed mathematically by the following equation (1):

$$\Psi = \frac{2\pi d_y}{\lambda}\sin\theta\sin\varphi + \frac{2\pi d_z}{\lambda}\cos\theta - 2\pi k,\ k = 0, \pm 1, \pm 2, \ldots, \quad (1)$$

wherein:
$d_y$ is the projection of the inter-element baseline vector onto the y-axis,
$d_z$ is the projection of the inter-element baseline vector onto the z-axis,
$\lambda$ is the wavelength of the impinging signal,
$\varphi$ and $\theta$ are the azimuth and zenith angles of arrival respectively, and
k is an integer set to the value that makes the overall phase difference come out in the range of $\pm\pi$.

This equation is easily modified to a more instructive form by substituting Y for $\sin\theta\sin\varphi$ and Z for $\cos\theta$:

$$\psi = \frac{2\pi d_y}{\lambda}Y + \frac{2\pi d_z}{\lambda}Z - 2\pi k \quad (2)$$

The two quantities Y and Z are recognized respectively as the y-axis and the z-axis direction cosines. This last equation can be manipulated to either of the following two forms:

$$Z = -\frac{d_y}{d_z}Y + \frac{\lambda}{2\pi d_z}(\psi + 2\pi k)\ \ d_z \neq 0 \quad (3a)$$

or $$Y = \frac{\lambda}{2\pi d_y}(\psi + 2\pi k)\ \ d_z = 0 \quad (3b)$$

Both of these expressions are each an equation of a straight line or more precisely each these equations defines a set of straight lines, one line for each value of the integer k. The lines are sometimes referred to as Hanson trajectories.

While it is true that physically the values of $\sin\varphi\sin\theta$ and $\cos\theta$ are both restricted to the range of $\pm 1$, there is no theoretical reason why Y and Z must be so restricted as long as it is recognized that values of Y or Z outside of this range to not correspond to physically observable angles. Indeed, the only physically observable values of Y and Z must lay on or inside a unit circle centered on the origin in Y-Z space or direction cosine space (see FIG. 2).

Looking back at Eq. 3a just above, it is seen that whenever $d_z$ is not exactly zero, the slope of the lines defined by this equation is $$\text{slope} = -\frac{d_y}{d_z}$$

while the z-axis offset for a particular value of the ambiguity integer is $$\text{offset} = \frac{\lambda}{2\pi d_z}(\psi + 2\pi k).$$

Whenever $d_z$ is exactly zero, the Hanson trajectories are parallel to the Y-axis, while whenever $d_y$ is exactly zero the Hanson trajectories are parallel to the Z-axis. The perpendicular distance between adjacent trajectories is $\lambda/d$, $$d = \sqrt{d_y^2 + d_z^2}$$

and should the distance between the two antennas increase, the ratio of $\lambda/d$ decreases and the distance between adjacent trajectories becomes less as well, assuming the signal wavelength remains constant. Contrary-wise, should the distance between the two antennas decrease, the distance between adjacent trajectories becomes greater. Should the ratio of $d_y$ to $d_z$ change, then the slopes of the trajectories change.

FIG. 2 is the Hanson Ambiguity Diagram for the pair of interferometer elements shown in the inset in the upper left corner. The interferometer array design process that is the subject of this invention begins by placing three antenna elements on their common mounting surface and then constructing either the Hanson ambiguity diagram for a strictly coplanar array or the Hanson-Workman ambiguity diagram for either a coplanar or a non-coplanar array. This three element ambiguity diagram identifies a set of angle ambiguities that must be removed with the addition of subsequent antenna elements to the array. As these subsequent elements are added to the array, the corresponding ambiguity diagram is expanded to include the intersection sets that arise with the additional phase differences being included in the system of diophantine equations that fully describe the operation of the interferometer system. Both types of ambiguity diagrams serve as geometrical techniques to conveniently solve this system of equations. While an exact solution to this system of equations is necessary, this solution by itself is not sufficient to effect an effective interferometer design. Beside the point of an exact solution, there exists a class of approximate solutions referred to here as "near-misses" that under some very real world circumstances can be mistaken for the desired exact solution. It is here that the method of the invention using the Hanson and Hanson-Workman ambiguity diagrams provides considerable insight into how to arrive at an operationally useful interferometer design.

Coplanar Array Design Method Using Hanson Ambiguity Diagrams

Using this concept, the performance of a complete array can be assessed including the issue of the existence or absence of irresolvable angle ambiguities. With a total of n antennas, there are n-l unique phase differences each creating a Hanson ambiguity trajectory set. The design process begins with two pairs of antennas placed at initial trial positions on the y-z plane. In this and all subsequent examples, the antenna elements are illustrated as circular apertures although there is not requirement that antenna elements in phase comparison interferometers be exclusively circular. Apertures of almost any shape are permissible. However, it is highly desirable that all of the elements within a given array be as nearly identical as manufacturing tolerances will allow.

Each pair may consist of two separate antennas, for a total of four, or they may share an antenna in common requiring a total of only three. Where the individual lines of the two sets of trajectories intersect, they form a two dimensional lattice of points only one of which corresponds to the true position of the emitter in direction cosine space.

FIG. 3 illustrates the lattice of points created by the intersection of two sets of Hanson ambiguity trajectories of the two antenna pairs illustrated in the inset in the upper left corner. As depicted in FIG. 3, this proper direction cosine is at the origin of the Y-Z coordinate system corresponding to an emitter positioned out along the positive X axis (emitters are assumed to occupy the space "in front" of the Y-Z plane, that for which X is always positive). At his stage the Hanson ambiguity diagram in FIG. 3 shows nineteen irresolvable angle ambiguities inside the unit circle of visibility. Additionally, many more angle ambiguities falling outside of the unit circle of visibility are also depicted in FIG. 3. It is quite possible that angle ambiguities that fall outside of the unit circle of visibility when the proper direction of arrival corresponds to Y=0 and Z=0 will ultimately find their way inside this circle when the proper direction of arrival is nearer the edge of the circle. To ensure that all possible angle ambiguities are seen, the ambiguity diagram must be made at least twice as large as the diameter of the unit circle.

The next step is to judiciously add a fourth antenna to the array depicted in FIG. 3 in such a way that the number of irresolvable angle ambiguities is reduced, the intent being to effect a significant reduction in the number of irresolvable angle ambiguities. A hypothetical trajectory corresponding to $k_3=0$ is placed on the diagram cutting across at some oblique angle and passing through the point at the center of the lattice. This allows alternative angles for this trajectory to be assessed as well as the number and placement of remaining irresolvable ambiguities. It is also important that inter-element spacing is more carefully considered at this point. A spacing chosen too large may well result in too few ambiguities being excluded, while a spacing chosen too small may not be compatible with the antenna aperture dimensions. FIG. 4 illustrates how a well-chosen position for a fourth element can reduce the large number of irresolvable ambiguities in FIG. 3 to a mere five. In addition, several irresolvable angle ambiguities outside of the unit circle are seen to remain. Several "near-miss" intersections are also revealed where three trajectories pass very close to one another without intersecting at a single common point; a typical near-miss is encircled in FIG. 4. When there are but three sets of Hanson trajectories involved, each of the three pairs of trajectories form a separate point of intersection at a near-miss, and the three intersection points form a simple triangle. Near-miss triangles with small areas are more troublesome in error prone circumstances then those with large areas; every combination of three Hanson trajectories form such a triangle but the included triangular area of some combinations is so large that a "near-miss" can not be said to have occurred. Consideration of the impact of such near-miss intersections is important in the design consideration because of the very real possibility that thermally induced electronic noise and other system phase errors may cause these near-misses to sometimes be mistaken as the proper choice for the direction cosine pointing at the emitter.

At this point it may be necessary or perhaps desirable to adjust the positions of one or more antennas, recalculate and re-plot all Hanson trajectories looking for better overall performance (e.g., lens irresolvable ambiguities). As yet all irresolvable ambiguities have not been eliminated but that goal follows in the next step. With four antennas there are six degrees of freedom (i.e., spacing), the angular position as well as the radial position of three of the four antennas relative to the fourth. To the extent allowed by the element dimensions (i.e. diameter) better overall ambiguity resolution performance is usually achieved by bringing the elements closer together. This widens the distance between the individual lines within a trajectory set, increasing the distances between the early stage irresolvable ambiguities. This in turn will likely make it easier to find positions for additional antenna elements that eliminate irresolvable ambiguities while at the same time avoiding the adverse impacts of near-misses intersections.

Substantially increasing the operating RF frequency will very likely render the performance of the array unacceptable. To do so could cause the number of irresolvable ambiguities to increase and the distances between these ambiguity points to decrease, making it much more likely that irresolvable ambiguities originally residing outside of the unit circle of visibility will fall inside. Additionally, the number and character of near-misses will change for the worse, i.e. additional near-misses will rise and the area inside the irregular polygon formed by the intersecting Hanson trajectories at a near-miss will decrease.

FIG. 4 illustrates the Hanson ambiguity diagram for the four element interferometer array in the inset in the upper left corner showing that the nineteen irresolvable angle ambiguities seen in FIG. 3 have been reduced to only three points P1, P2, P3 by the addition of the fourth antenna.

In the final step yet a fifth antenna is added as shown in FIG. 5. Here the inter-element baseline vector is horizontal and accordingly the Hanson ambiguity trajectories are oriented vertically. As seen in FIG. 5, the center intersection is picked out by this ambiguity trajectory set and all of the other trajectories of this set are arranged to avoid intersecting with the remaining irresolvable ambiguities inside the unit circle of visibility. There are irresolvable ambiguities that do still exist but these are outside of the unit circle sufficiently far that should the emitter signal arrive from a location near the edge of the field of visibility, these remaining ambiguities will not be pulled inside the unit circle.

This design is to be understood as only an example of the method of arranging the antennas so that irresolvable angle ambiguities are minimized. The presence of the "near-misses" renders the design of this example in need of adjustment or possibly abandonment in favor of a different design, one that, nevertheless, is accomplished using the methods described herein.

FIG. 5 is the Hanson ambiguity diagram for the completed interferometer design for the five element interferometer array in the inset in the upper left corner that exhibits no irresolvable angle ambiguities inside the unit circle of visibility.

The Hanson ambiguity diagram is particularly well suited to the purpose of assessing the effects of "near-miss" intersections. The effects of thermal noise and other system phase errors may force the Hanson ambiguity trajectories involved in these near-misses to move even closer together than they otherwise would be in no-error conditions. Likewise, the Hanson ambiguity trajectories, (one trajectory from each set), for the one proper intersection will undoubtedly be forced apart into multiple, two line intersections under these error prone conditions. In these circumstances, there may well be no one common point where one trajectory from each of the several sets intersect; in effect, the proper intersection becomes merely another near-miss among several near-misses. For those skilled in the art of interferometric signal processing there are available a number of pre-existing methods for deciding which of the several near-miss sets is the most likely to be the proper set. Azzarelli refers to these methods as "tightest cluster estimation" and then goes on to describe in detail a method similar to a pre-existing technique based upon minimizing the sum of the perpendicular miss distances between the chosen solution point and the several Hanson trajectories.

The designer of an interferometer array must take care to ensure that under error prone conditions, the effects of noise and other phase errors do not (or only very infrequently) make it possible for decision process to mistakenly choose a near-miss rather than the "proper" set of intersections.

Finally, it must be said that as illustrated antennas #2, #3, #4 and #5 are referenced to antenna #1 as their phase reference. There is no reason for this relationship other than convenience of illustration. It is quite possible to design interferometers so that the several antennas are interrelated in almost any conceivable manner so long as there is no attempt to employ more than N-1 phase differences, N being the total number of antenna elements in the interferometer array. The present Hanson ambiguity diagram method for assessing the arrangement of antennas works equally as well in these cases as it does in the situation illustrated above.

Non-Coplanar Array Design Method Using Hanson-Workman Ambiguity Diagrams

The Hanson ambiguity diagram offers an intuitive as well as a visual method to adjust the slopes and lengths of the several inter-element baselines for a coplanar interferometer array. The equivalent three dimensional diagram—the so-called Hanson-Workman ambiguity diagram—is itself an inherently three dimensional geometrical construct and as such it is somewhat less visual. Its value lies in the fact that it leads to a relatively easily implemented computer algorithm that can be used to develop two dimensional projections of the several objects found in a fully three dimensional Hanson-Workman ambiguity diagram.

Optimizing the design of a non-coplanar interferometer array begins in much the same manner as the design of a coplanar array. A suitable portion of complex curved surface (see FIG. 6) is selected onto which the array antennas are to be mounted. The first antenna is placed on this surface so that it is more or less positioned in the center of this area, while the second and third antennas are positioned near the first to form separate inter-element baselines. The lengths of these two baselines may be identical or they may be unequal but in general these two antennas must be positioned so that the two baselines are not collinear. Two separate baselines give rise to two sets of interferometer planes and consequently two sets of circles of intersection of these planes with the direction cosine sphere, all of which is described in the co-pending application. These circles are referred to here as ambiguity circles and the composite of several circles from a single non-coplanar interferometer array is referred to as a Hanson-Workman ambiguity diagram. It must be said at this point that when the co-pending application was filed, it was thought that mathematics leading from measured phase differences to the intersection of two or more ambiguity circles on the surface of the direction cosine sphere would cause these intersections to properly occur in the hemisphere of the direction cosine sphere corresponding to the positive portion of the x-axis; it is now understood that these intersections occur in the opposite hemisphere; the y-axis and the z-axis direction cosine are also sign (+/−) inverted as well.

The next step is to determine the points of intersection of the various members of each set of ambiguity circles in the manner similar to the method described in co-pending application. To begin this process a convenient direction of arrival is chosen and the two phase differences, $\psi_1$ and $\psi_2$, are calculated. While there is no correct direction of arrival that must be used for these calculations, it would seem that simplicity is best served if the chosen direction arrival corresponds to that for which a radiating emitter is positioned along the positive x-axis. In this case then $\phi=0°$ and $\theta=90°$.

FIG. 6 illustrates the Hanson-Workman ambiguity diagram for three antennas arranged as illustrated in the inset schematic diagram and as indicated in the table.

Even though one definition of the Hanson-Workman ambiguity diagram describes a-three dimensional figure consisting of a sphere and intersecting circles laying on the surface of this sphere, this analysis uses the two dimensional projection of the sphere and the circles onto one of the three principle planes; the y-z plane will be chosen for this role in this description. In this way the concept of the intersecting, three dimensional objects is transformed into something that will appear more like the usual, two dimensional Hanson ambiguity diagram. The sphere is transformed into a unit circle and the ambiguity circles are transformed into ellipses. Multiple baseline ambiguities are still depicted as points where the intersecting ambiguity circles project onto the y-z plane. The most distinctive difference between the two concepts is that of the existence of invisible space. The two dimensional Hanson ambiguity diagram not only allows for a method to directly visualize invisible space, but makes full use of this invisible space to depict ambiguities that are theoretically located in this invisible region but under the influence of electronic noise and other phase error mechanisms, may fall inside the circle of visibility in a practical interferometer. Invisible space can not be explicitly depicted in a Hanson-Workman ambiguity diagram, although ambiguity circles with imaginary radii can be said to "exist"; the word imaginary here refers to a $\sqrt{-1}$ multiplier to the numerical value for the radius of such an invisible ambiguity circle. Ambiguity circles for which $R\approx0.9\sqrt{-1}$ may well be forced back onto the surface of the direction cosine sphere by the effects of electronic noise or other phase error mechanisms and result in one or more ambiguities that would not exist under error-free operation.

FIG. 6 illustrates three antennas installed on the complex curved surface along with the y-z projection form of the Hanson-Workman ambiguity diagram for the two ambiguous phase differences $\psi_1$ and $\psi_2$; the exact location of each antenna element is shown in the inset box beneath the illustration of the mounted antennas. The ambiguity integers associated with each of the several ambiguity circles are shown placed around the periphery of the y-z plane projection of the direction cosine sphere immediately next to the corresponding elliptical projection of the several ambiguity circles. For the purposes of this illustration the signal carrier frequency was chosen as 12.0 GHz where the wavelength is almost exactly one inch. For the given antenna orientations and the signal wavelength, the two measured phase differences turn out to be $\psi_1=-176.99°$ and $\psi_2=+137.25°$. Besides the proper intersection at x=−1.0, y=0 and z=0, there are eighteen ambiguous alternatives, i.e., irresolvable ambiguities at this point.

To continue, this method of interferometer design demonstrates the usefulness of the Hanson-Workman ambiguity diagram as the basis for making decisions regarding how to place the antennas within the array. The three element array in FIG. 6 was chosen specifically and exclusively to illustrate the elliptical projections of the several ambiguity circles. Accordingly, it is convenient to begin anew with a different three element array. The three element array shown in FIG. 7 is the starting point for the design of a complete array. Nevertheless, as in FIG. 6 the x-y-z coordinates of the three antennas are listed in the inset box. Moreover, to decrease the confusion of portraying dozens of ellipses in the Hanson-Workman ambiguity diagram, it is convenient to merely show the y-z plane projections of the common points of intersection of the many ambiguity circles. As can easily be counted in FIG. 7, there are a total of eighteen ambiguous choices for Y=sin φ sin θ and Z=cos θ that produce the same two measured phase angles—$\psi_1$=+91.5° and $\psi_2$=0°—including the correct choice of φ=0° and θ=90° corresponding to Y=0 and Z=0. Even though the elliptical projections of the several ambiguity circles are not shown in FIG. 7, the general outline of the ellipses are revealed by the positions of the common points of intersection.

The next step, then, is to locate additional antenna elements within the array. The strategy here is exactly as it was with the two dimensional, coplanar array design method: add additional antennas to the array at positions chosen to avoid placing intersection points near any remaining ambiguities or near-miss point collections. In the present case the results of adding just a fourth antenna to the three shown in FIG. 7 are shown in FIG. 8. The fourth antenna has failed to completely remove all irresolvable ambiguities, and it has left ten very serious near-miss pairs, all of which must be dealt with by adding a fifth and possibly additional antennas beyond the fifth.

FIG. 7 illustrates the Hanson-Workman ambiguity diagram for the three element non-coplanar test array in the inset that will serve as the basis for illustrating the design process that results in a completely unambiguous interferometer array.

In FIG. 7, elements 1 and 2 are phase-paired together as are elements 2 and 3. Phase-paired elements are any two interferometer antenna elements between which an actual phase measurement is extracted. The circuitry connecting these two elements through two separate channels of the radio receiver leads directly to a single phase comparator. Herein two phase-paired antenna elements will be denoted by including a straight line arrow between the centers of the two elements. The element intended to be the phase reference of the pair has the tail of the arrow positioned at its center.

In FIG. 8, these two phase-pair relationships are retained and antenna #4 is phase-paired with antenna #3. To the eighteen intersections—depicted with a black circular dot ●—from the $\psi_1$-$\psi_2$ intersection set the Hanson-Workman ambiguity diagram in FIG. 8 shows the thirty-nine intersections contained in the $\psi_2$-$\psi_3$ set all depicted with a open square dot □; at φ=0° and θ=90°, $\psi_2$=0° and $\psi_3$=45.75°. A careful examination of this figure reveals that besides the actual angle of arrival at φ=0° and θ=90°, there are two near-miss intersections (circled) that are essentially irresolvable ambiguities and as many as nine other near-miss intersections.

Three sets of ambiguity circles intersections can be constructed from three unique phase differences and the complete Hanson-Workman ambiguity diagram would include these three distinct sets of intersections. With N antennas in the interferometer array, a total of ½(N−1)2−½(N−1) sets of ambiguity circle intersections can be constructed.

However, since the information being extracted from this diagram is the existence (or not) of either irresolvable ambiguities or near-miss pairs, it is not necessary to include all possible intersection sets. The information extracted from first two intersection sets contains all of the information ultimately available from the three phase angles. Including the third intersection set in the diagram only duplicates information that is already in evidence from the first two sets.

FIG. 8 illustrates adding antenna #4 to the three element array of FIG. 7 resulting in two irresolvable angle ambiguities (circled) and ten troublesome near-miss pairs.

In FIG. 9, a fifth antenna element is added to the array, in this case immediately to the left of element #4. With this element in place the ambiguity circle intersection set from phase differences $\psi_3$-$\psi_4$ are added to the Hanson-Workman ambiguity diagram. At φ=0° and θ=90°, $\psi_3$=45.75° and $\psi_4$=0°. These new intersections, a total of ten, are depicted in FIG. 9 as triangular-shaped dots—Δ. As can be seen in FIG. 9, none of these triangles fall particularly near either of the irresolvable ambiguities or any of the ten near-miss pairs shown in FIG. 8. Indeed, the closest one of these triangular dots falls to a near-miss pair, a black dot and a square dot together, is some 7.7° spatial. It is a matter of design choice of the array designer, but it is usually preferably to arrange the array elements so that the spatial angular separation between at least one pair of intersections in each near-miss cluster is at least four times the expected direction finding accuracy.

At this point, this five element array is subjected to one final test, a test intended to determine if moving the direction of arrival to a point near the extreme edge of the field of view results in the reappearance of either irresolvable ambiguities or tightly clustered near-misses. In this example the position of the emitter was moved from it current position 100,000 inches out along the positive x-axis to a location where the direction of arrival will appear to come from φ=80° and θ=45°. When this test was completed, one set of three near-miss intersections was found. So tightly clustered, when this group of three intersections was first seen, it was thought to be a truly irresolvable ambiguity rather than just a "near-miss". The results of this test are illustrated in FIG. 10. This near-miss cluster is identified-in FIG. 10 by being encircled. It is located some 42.95° from the center of the field of view and undoubtedly represents a significant source of ambiguity trouble in an operational system.

FIG. 9 illustrates adding the fifth element to the array eliminating the two irresolvable ambiguities depicted in FIG. 8 as well as all near-miss pairs without reintroducing any additional irresolvable ambiguities.

FIG. 10 illustrates the results of an "edge of field of view" test conducted to see if irresolvable ambiguities and/or near-miss clusters come into view as the direction of arrival angle is scanned away from the exact center of the y-z plane. One near-miss cluster (circled) was found.

At this point the design process would make several attempts to adjust the positions of one more of the five elements in the array in an attempt to eliminate this near-miss ambiguity. However, in this case this effort was quickly abandoned for the purposes of illustrating the effects of adding a sixth element to the array.

A sixth element was located beneath antenna #4 on the y-axis as shown in FIG. 11. Also shown in FIG. 11 are the schematic diagram of the complete six element array and its Hanson-Workman ambiguity diagram for φ=0° and θ=90°. The additional points of intersection, depicted as diamond-shaped dots ◊, are the results of combining the ambiguity circles from the phase difference between elements 4 and 5, $\psi_4$ with those of the phase difference between elements 5 and 6, $\psi_5$. Two of these diamond-shaped dots are found to fall in the midst of loosely clustered three intersection sets from the five element array; however this added data point is unlikely to upset a well designed ambiguity resolution algorithm looking for a cluster of points that would all have identical direction cosines were it not for the effects of phase noise.

This six element array was then subjected to the field of view edge test exactly as the five element array had been previously and, as expected, the sixth element did indeed eliminate the near-miss found in the Hanson-Workman ambiguity diagram for the five element array.

FIG. 11 illustrates the completed design of a six element interferometer array. The intersection points for the fourth and five baselines are depicted as diamond-shaped dots.

It should be rather apparent that the selection of the positions for the individual elements in order to achieve all of the design objectives involves an iterative approach. Both the Hanson and the Hanson-Workman ambiguity diagrams greatly facilitate this process leading to a successful design much more rapidly than would otherwise be possible.

Beyond using either the Hanson or the Hanson-Workman ambiguity diagrams as design tool, it is sometimes helpful to locate the elements at the lattice points of a square lattice for a coplanar array or a cubic lattice for a non-coplanar array. Adjacent points within the lattice should be set to a distance equal to or less than half a wavelength at the highest operating RF frequency. Viewing the inter-element baseline as a three dimensional vector, such inter-element vectors can be expressed in the following manner:

$$d_i = N_{xi}\hat{i} + N_{yi}\hat{j} + N_{zi}\hat{k}$$

For a two dimensional coplanar array this inter-element baseline vector $d_i$ could also be expressed by this relationship just with $N_{xi}$ set equal to 0 for every baseline. Should this strategy be used, it is important to take full advantage of the lattice structure by locating some elements an odd number intervals apart, while others can be spaced at even number intervals of lattice points. Should the distances between elements all be chosen as even multiples of lattice points, the dimensionality of the lattice is thereby reduced by at least a factor of two with the result being that elements will be spaced at multiples of a full wavelength at the highest operating RF frequency rather than multiples of half of this shortest wavelength. Unfortunately for many three dimensional circumstances this strategy may be virtually impossible to realize for reasons related to nature of the structure onto which the array is to be mounted.

A second, possibly helpful strategy is to position the elements so that the radial distances between phase-paired elements are multiples of a half wavelength at the highest operating RF frequency. Again some elements should be spaced at odd intervals, while others are spaced at even intervals. While this strategy will ensure that the phase-paired elements are positioned to meet this strategy, the distances between any two arbitrarily chosen elements will undoubtedly fail to meet this criteria.

Thus, one embodiment of the invention includes an iterative method of arranging a plurality of transducers (particularly non-collinear, non-coplanar spaced antenna elements) having phase errors in order to use the antenna elements to determine a direction of arrival of a signal (radiation) emitted by a source. In this iterative method, a set of trajectories for the plurality of antenna elements is determined. The relative position of the antenna elements is then modified (e.g., by modifying the spacing) and a modified set of trajectories for the plurality of antenna elements after modifying the position is determined. The number of ambiguities corresponding to the set of trajectories is compared to the number of ambiguities corresponding to the modified set of trajectories. The antenna elements are arranged according the position which corresponds to less ambiguities. The resulting antenna array also embodies the invention.

The iterative method may instead include and may also include modifying the preset number of the antenna elements (e.g., adding or removing antenna elements from the array) and determining a modified set of trajectories for the plurality of antenna elements after modifying the preset number. The number of ambiguities of the set of trajectories before modifying is compared with the number after modifying to determine which has less ambiguities. The array is then assembled with a number of antenna elements which number which corresponds to less ambiguities. The resulting antenna array also embodies the invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A method of arranging a plurality of spaced transducers having phase errors in order to use the transducers to determine a direction of arrival of a signal emitted by a source, said method comprising:
    determining a set of trajectories for the plurality of transducers and determining the number of ambiguities corresponding to the set of trajectories;
    modifying the relative position of the transducers;
    determining a modified set of trajectories for the plurality of transducers after modifying the position and determining the number of ambiguities corresponding to the modified set of trajectories;
    comparing the number of ambiguities corresponding to the set of trajectories to the number of ambiguities corresponding to the modified set of trajectories; and
    arranging the transducers according the position which corresponds to less ambiguities.

2. The method of claim 1 wherein modifying the relative position comprises modifying the spacing by changing the relative radial positions of one or more of the transducers and/or by changing the relative angular positions of one or more of the transductions.

3. The transducer array resulting from the method of claim 1.

4. The method of claim 1 wherein the transducers are antennas mounted on a surface of an aircraft.

5. The method of claim 1 wherein the transducers are selected from the following: antennas, rf sensors, sonaphones, sound sensors, seismic sensors, acoustic wave sensors and/or pressure sensors.

6. The method of claim 1 wherein the determining a set of trajectories comprises using at least one of a Hanson ambiguity diagram, a Hanson-Workman ambiguity diagram, a two dimensional projection of the transducers and the points of intersection of each set of ambiguity circles of the transducers.

7. The method of claim 1 further comprising a method for determining a direction of arrival of a signal emitted by a source, said method comprising:

receiving the emitted signal with a first transducer of the arranged transducers and providing a first transducer output signal corresponding to the emitted signal received by the first transducer;

receiving the emitted signal with a second transducer of the arranged transducers, said second transducer spaced a distance $D_{12}$ from the first transducer and providing a second transducer output signal corresponding to the emitted signal received by the second transducer;

determining a first set of interferometer planes corresponding to a phase difference between the first transducer output signal and the second transducer output signal, said phase difference being a function of the distance $D_{12}$; and providing output information corresponding to a direction of arrival of the emitted signal relative to the first and second transducers, wherein the output information is a function of an intersection of the set of interferometer planes with a direction cosine sphere.

8. The method of claim 1 wherein modifying the relative position of the transducers comprises moving the direction of arrival to a point near the edge of the field of view to determine if there are other ambiguities or any other near-misses.

9. The method of claim 1 further comprising:
modifying the preset number of the transducers;
determining a second modified set of trajectories for the plurality of transducers after modifying the preset number and determining the number of ambiguities corresponding to the second modified set of trajectories;
comparing the number of ambiguities corresponding to the set of trajectories to the number of ambiguities corresponding to the second modified set of trajectories to determine which set has less ambiguities; and
arranging an array of the transducers having a number of transducers which corresponds to the set with less ambiguities.

10. The method of claim 9 wherein modifying comprises adding one or more transducers in positions relative to the other transducers which minimizes placing intersection points of the corresponding trajectories near any remaining ambiguities or near-miss point collections.

11. A method of arranging a plurality of spaced transducers having phase errors in order to determine a direction of arrival of a signal emitted by a source, said method comprising:
determining a set of trajectories for a preset number of the plurality of transducers and determining the number of ambiguities corresponding to the set of trajectories;
modifying the preset number of the transducers;
determining a modified set of trajectories for the plurality of transducers after modifying the preset number and determining the number of ambiguities corresponding to the modified set of trajectories;
comparing the number of ambiguities corresponding to the set of trajectories to the number of ambiguities corresponding to the modified set of trajectories to determine the more tightly grouped set of trajectories; and
arranging an array of the transducers having a number of transducers which corresponds to the set with less ambiguities.

12. The transducer array resulting from the method of claim 11.

13. The method of claim 11 further comprising:
modifying the relative position of the transducers;
determining a second modified set of trajectories for the plurality of transducers after modifying the position and determining the number of ambiguities corresponding to the second modified set of trajectories;
comparing the number of ambiguities corresponding to the set of trajectories to the number of ambiguities corresponding to the second modified set of trajectories to determine the set with fewer ambiguities; and
arranging the transducers according the position which corresponds to the set with less ambiguities.

14. The method of claim 13 wherein modifying the relative position comprises modifying the spacing by changing the relative radial positions of one or more of the transducers and/or by changing the relative angular positions of one or more of the transductions.

15. The method of claim 13 wherein modifying the relative position of the transducers comprises moving the direction of arrival to a point near the edge of the field of view to determine if there are other ambiguities or any other near-misses.

16. The method of claim 11 wherein the transducers are antennas mounted on a surface of an aircraft.

17. The method of claim 11 wherein the transducers are selected from the following: antennas, rf sensors, sonaphones, sound sensors, seismic sensors, acoustic wave sensors and/or pressure sensors.

18. The method of claim 11 wherein the determining a set of trajectories comprises using at least one of a Hanson ambiguity diagram, a Hanson-Workman ambiguity diagram, a two dimensional projection of the transducers and the points of intersection of each set of ambiguity circles of the transducers.

19. The method of claim 11 further comprising a method for determining a direction of arrival of a signal emitted by a source, said method comprising:
receiving the emitted signal with a first transducer of the arranged transducers and providing a first transducer output signal corresponding to the emitted signal received by the first transducer;
receiving the emitted signal with a second transducer of the arranged transducers, said second transducer spaced a distance $D_{12}$ from the first transducer and providing a second transducer output signal corresponding to the emitted signal received by the second transducer;
determining a first set of interferometer planes corresponding to a phase difference between the first transducer output signal and the second transducer output signal, said phase difference being a function of the distance $D_{12}$; and
providing output information corresponding to a direction of arrival of the emitted signal relative to the first and second transducers, wherein the output information is a function of an intersection of the set of interferometer planes with a direction cosine sphere.

20. The method of claim 10 wherein modifying comprises adding one or more transducers in positions relative to the other transducers which minimizes placing intersection points of the corresponding trajectories near any remaining ambiguities or near-miss point collections.

* * * * *